United States Patent
Carrano et al.

(10) Patent No.: US 9,682,378 B1
(45) Date of Patent: Jun. 20, 2017

(54) MATING ADAPTOR FOR COUPLING A POINT-OF-CARE DIAGNOSTIC CARTRIDGE TO A COMPUTING DEVICE

(71) Applicant: Paratus Diagnostics, LLC, Austin, TX (US)

(72) Inventors: John Carrano, Austin, TX (US); Roland Schneider, Austin, TX (US); John Jacob Carrano, Austin, TX (US)

(73) Assignee: PARATUS DIAGNOSTICS, LLC, Austin, TX (US)

(*) Notice: Subject to any disclaimer, the term of this patent is extended or adjusted under 35 U.S.C. 154(b) by 0 days.

(21) Appl. No.: 14/962,998

(22) Filed: Dec. 8, 2015

(51) Int. Cl.
*B01L 9/00* (2006.01)
*G01N 21/00* (2006.01)
*B01L 7/00* (2006.01)
*G01N 35/00* (2006.01)

(52) U.S. Cl.
CPC .......... *B01L 9/00* (2013.01); *B01L 7/00* (2013.01); *G01N 35/00871* (2013.01); *B01L 2200/02* (2013.01); *B01L 2200/04* (2013.01); *B01L 2200/10* (2013.01); *B01L 2300/023* (2013.01); *B01L 2300/0627* (2013.01); *B01L 2300/0809* (2013.01); *B01L 2300/18* (2013.01)

(58) Field of Classification Search
CPC ........ G01N 21/00; G01N 15/06; G01N 35/00; B01L 9/00
USPC ........ 422/63, 68.1, 560, 561, 566, 501, 502, 422/503, 504; 436/43, 164
See application file for complete search history.

(56) References Cited

U.S. PATENT DOCUMENTS

| | | |
|---|---|---|
| 4,753,775 A | 6/1988 | Ebersole |
| 5,863,502 A | 1/1999 | Southgate |
| 6,645,758 B1 | 11/2003 | Schnipelsky |
| 7,267,799 B1 * | 9/2007 | Borich et al. ............ 422/82.05 |
| 8,249,547 B1 * | 8/2012 | Fellner .................... 455/404.1 |
| 8,318,439 B2 | 11/2012 | Battrell |
| 8,506,908 B2 | 8/2013 | Benn |
| 9,085,745 B2 | 7/2015 | Eckelberry |
| 2001/0045355 A1 * | 11/2001 | Gephart et al. ............ 204/400 |
| 2003/0073931 A1 * | 4/2003 | Boecker et al. ............ 600/573 |
| 2010/0120083 A1 | 5/2010 | Ritzen |
| 2010/0143963 A1 * | 6/2010 | Pollack et al. ............... 435/29 |
| 2011/0306859 A1 * | 12/2011 | Saldivar et al. ............ 600/365 |
| 2012/0164627 A1 | 6/2012 | Battrell |
| 2013/0142708 A1 | 6/2013 | Battrell |
| 2013/0157351 A1 * | 6/2013 | Ozcan et al. ............. 435/288.7 |
| 2013/0302787 A1 | 11/2013 | Agarwal |
| 2013/0337432 A1 | 12/2013 | Cook |
| 2014/0072474 A1 | 3/2014 | Kido |
| 2014/0286550 A1 * | 9/2014 | Beule et al. ................ 382/128 |
| 2015/0031412 A1 * | 1/2015 | Quilter et al. ............. 455/556.1 |
| 2015/0050719 A1 | 2/2015 | Bammesberger |

(Continued)

*Primary Examiner* — Brian J Sines
(74) *Attorney, Agent, or Firm* — McGuireWoods LLP (57) ABSTRACT

A mating adaptor for use in assaying a specimen includes an adaptor body having a first receiving area for receiving a computing device and a second receiving area for receiving a specimen delivery cartridge. The mating adaptor further includes an actuator for transmitting a mechanical actuation signal to initiate a fluidic process of a specimen delivery cartridge. The first receiving area includes a first connector corresponding to a computing device connector and the second receiving area includes a second connector corresponding to a specimen delivery cartridge connector.

15 Claims, 5 Drawing Sheets

(56) References Cited

U.S. PATENT DOCUMENTS

2015/0300957 A1 10/2015 Salsman
2015/0304555 A1* 10/2015 Ehrenkranz .................. 422/68.1

* cited by examiner

MATING ADAPTOR FOR COUPLING A POINT-OF-CARE DIAGNOSTIC CARTRIDGE TO A COMPUTING DEVICE

TECHNICAL FIELD

The present disclosure relates generally to the field of medical diagnostics and more particularly to in vitro medical diagnostic devices including point-of-care in vitro medical diagnostic devices.

BACKGROUND OF THE INVENTION

There is a recognized and compelling need for the rapid and accurate diagnosis of common infectious diseases in an out-patient setting. This need results from a rapidly emerging trend toward what is sometimes referred to as "patient centric care" in which convenience—along with better health outcomes and low-cost—becomes a key market driver.

The field of in vitro diagnostics is well established, with many manufacturers and a wide spectrum of products and technologies. The testing for infectious pathogens in human patient specimens is largely confined to centralized laboratory testing in Clinical Laboratory Improvement Amendment (CLIA) rated medium-complexity or high-complexity facilities. Commonplace techniques used in such laboratories include traditional culturing of specimens, immunological assaying using Enzyme-Linked Immunosuppressant Assay (ELISA), nucleic acid testing (such as polymerase chain reaction, PCR), and other methods.

SUMMARY

In accordance with a first illustrative embodiment, a mating adaptor includes an adaptor body having a first receiving area for receiving a computing device and a second receiving area for receiving a specimen delivery cartridge. The mating adaptor further includes an actuator for transmitting a mechanical actuation signal to initiate a fluidic process of a specimen delivery cartridge. The first receiving area includes a first connector corresponding to a computing device connector and the second receiving area includes a second connector corresponding to a specimen delivery cartridge connector.

In accordance with another illustrative embodiment, a system for implementing a diagnostic process includes a mating adaptor, a computing device, and a specimen delivery cartridge. The mating adaptor includes an adaptor body having a first receiving area for receiving the computing device and a second receiving area for receiving the specimen delivery cartridge. The first receiving area includes a first connector corresponding to a computing device connector. The second receiving area includes a second connector corresponding to a specimen delivery cartridge connector.

In accordance with another illustrative embodiment, a method for implementing a diagnostic process includes sliding a computing device into a first receiving area of a mating adaptor, and sliding a specimen delivery cartridge into a second receiving area of the mating adaptor. The step of sliding the computing device into the first receiving area includes coupling a data port of the computing device to a first connector of the mating adaptor, and the step of sliding the specimen delivery cartridge into the second receiving area comprises coupling a second data port of the specimen delivery cartridge to a second connector of the mating adaptor.

Other features and advantages of the present invention will be apparent from the accompanying drawings and from the detailed description that follows below.

BRIEF DESCRIPTION OF THE DRAWINGS

Illustrative embodiments of the present disclosure are described in detail below with reference to the attached figures, which are incorporated by reference herein, and wherein:

FIG. 2b is an end view of the specimen delivery cartridge of FIG. 2a;

FIG. 2c is a top view of the specimen delivery cartridge of FIG. 2a;

The illustrated figures are only exemplary and are not intended to assert or imply any limitation with regard to the environment, architecture, design, or process in which different embodiments may be implemented.

DETAILED DESCRIPTION

The conventional model for infectious disease diagnosis relies heavily on centralized laboratory testing (e.g. culture), which can often take two to four days to provide a reliable result. Applicant performed time-and-motion studies of medical practice and patient flow in the current model of infectious disease diagnosis and compared it to the new model relying on the devices described in this disclosure. A consequence of the conventional model is that patients are not necessarily properly diagnosed on their first visit; nor are they given the correct drug prescription. This results in money wasted on either incorrect or unnecessary prescriptions, inconvenience to patients owing to repeat visits, and even the potential for otherwise treatable illnesses to progress to more serious conditions requiring expensive hospital stays. In addition, it is noted that the over-prescription of antibiotics is not only a cost burden to the healthcare system, but perhaps more importantly may contribute to the increasing frequency of antibiotic resistant strains in the community, which is a national health concern.

There are some rapid diagnostic tests (RDTs) on the market today that are suitable for use in an out-patient setting. These RDTs, however, are simple "rule-in/rule-out" tests which do not necessarily inform clinical decision-making. Furthermore, many of these RDT's suffer from poor sensitivity and specificity, making the validity and clinical utility of their results dubious at best.

In diagnosing a patient, it is common for a physician to ask is whether an illness is the consequence of a bacterial or a viral pathogen. The present disclosure relates to a system that is able to provide that answer during the patient visit and with gold-standard accuracy. In this way, the correct diagnosis is obtained, and the best treatment option prescribed.

In point-of-care diagnostics for infectious disease, a premium is placed on the ability to achieve low-complexity and low-cost while substantially improving health outcomes. Further, to leverage the ubiquity of smartphones and other computing devices in common use globally, a mating adaptor is disclosed that allows for the use of a computing device, such as a smart phone, in connection with a mating adaptor and specimen delivery cartridge, to carry out a test for one or more pathogens. The mating adaptor accommodates the form factor and interfaces of popular computing devices (e.g., smart phones) by providing for a variety of interfaces. Each interface may equate to a customized adaptor that is designed to mate with a particular smartphone. However, the adaptor interfaces to the cartridge will generally be identical; meaning that the cartridge will fit to any of a variety of a range of adaptors that accommodate a corresponding range of smart phones or other computing devices.

The specimen delivery cartridge may be considered to be similar in some respects to the cartridge or "specimen delivery apparatus" described in earlier-filed patent application Ser. No. 13/918,877 entitled "Specimen Delivery Apparatus" submitted by applicant, which is hereby incorporated by reference.

Figure 1:
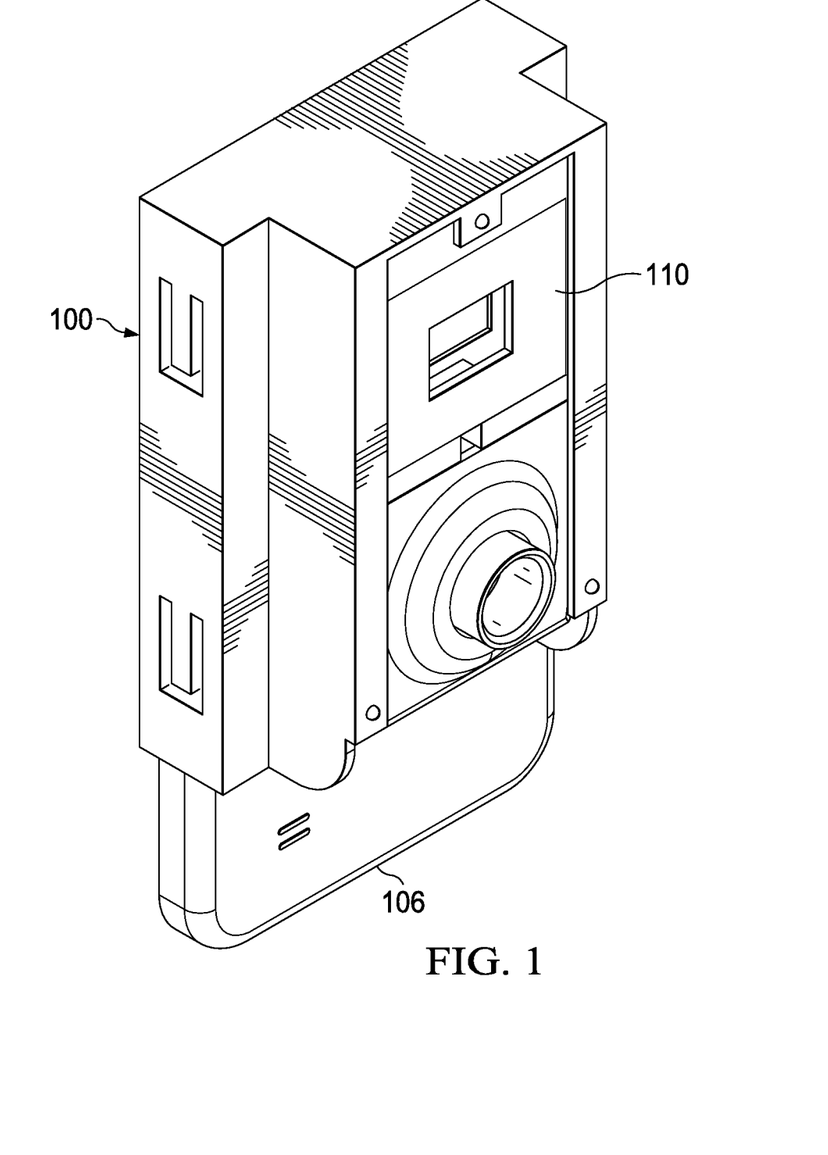
FIG. 1 is a perspective view of a mating adaptor coupling a computing device to a specimen delivery cartridge.
Figure 2A:
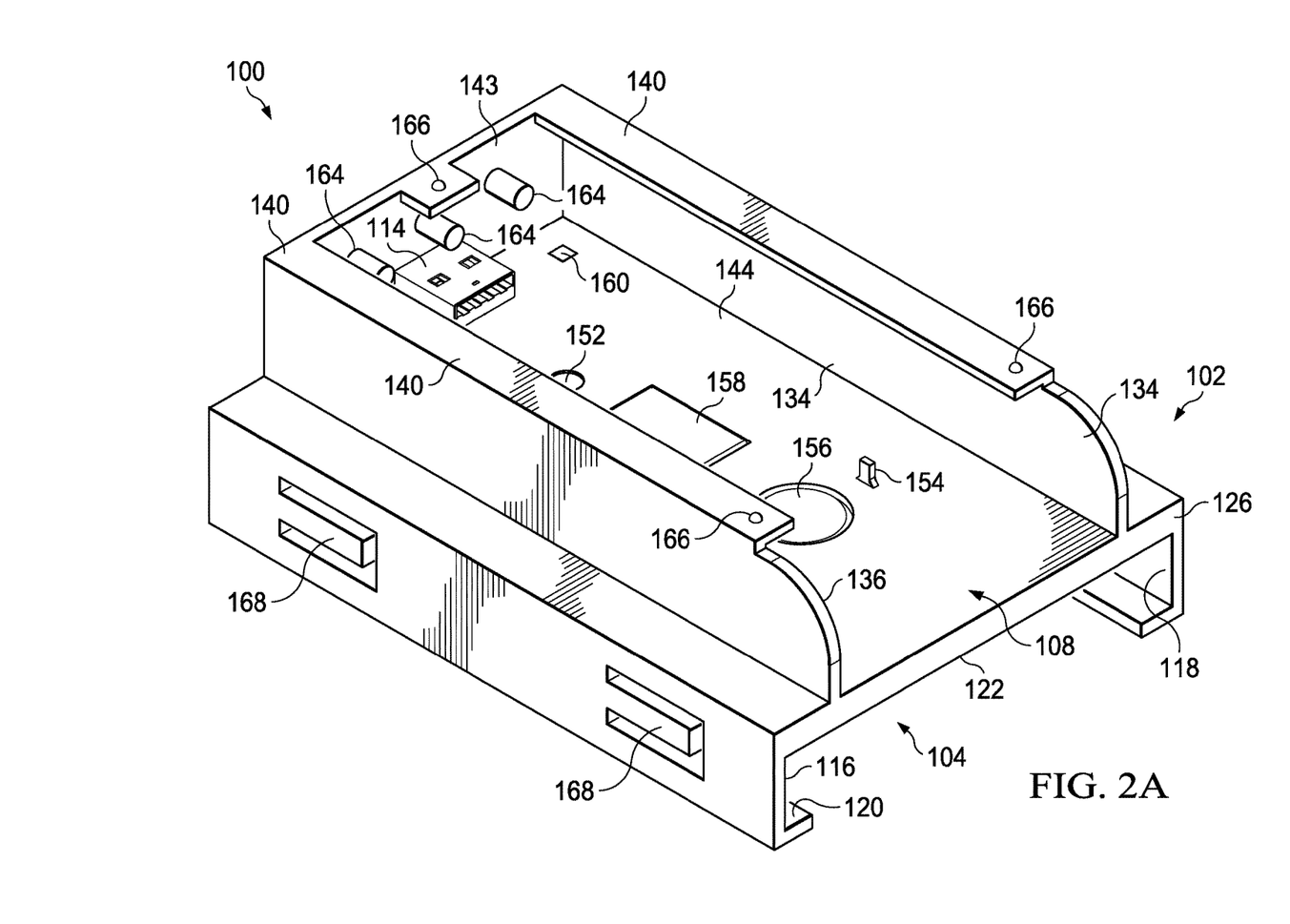
FIG. 2a is a perspective view of the mating adaptor of FIG. 1, showing the features of a receiving area that is configured to receive the specimen delivery cartridge.
Figure 2B:
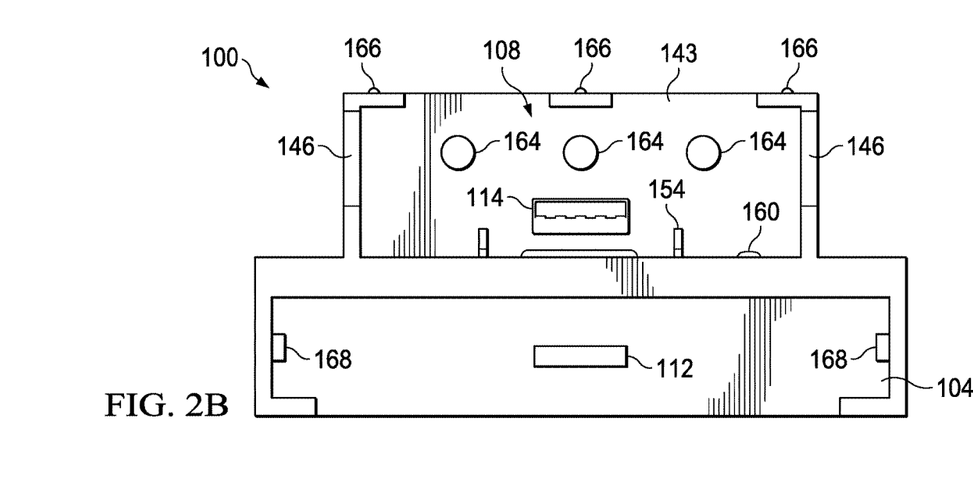
Figure 2C:
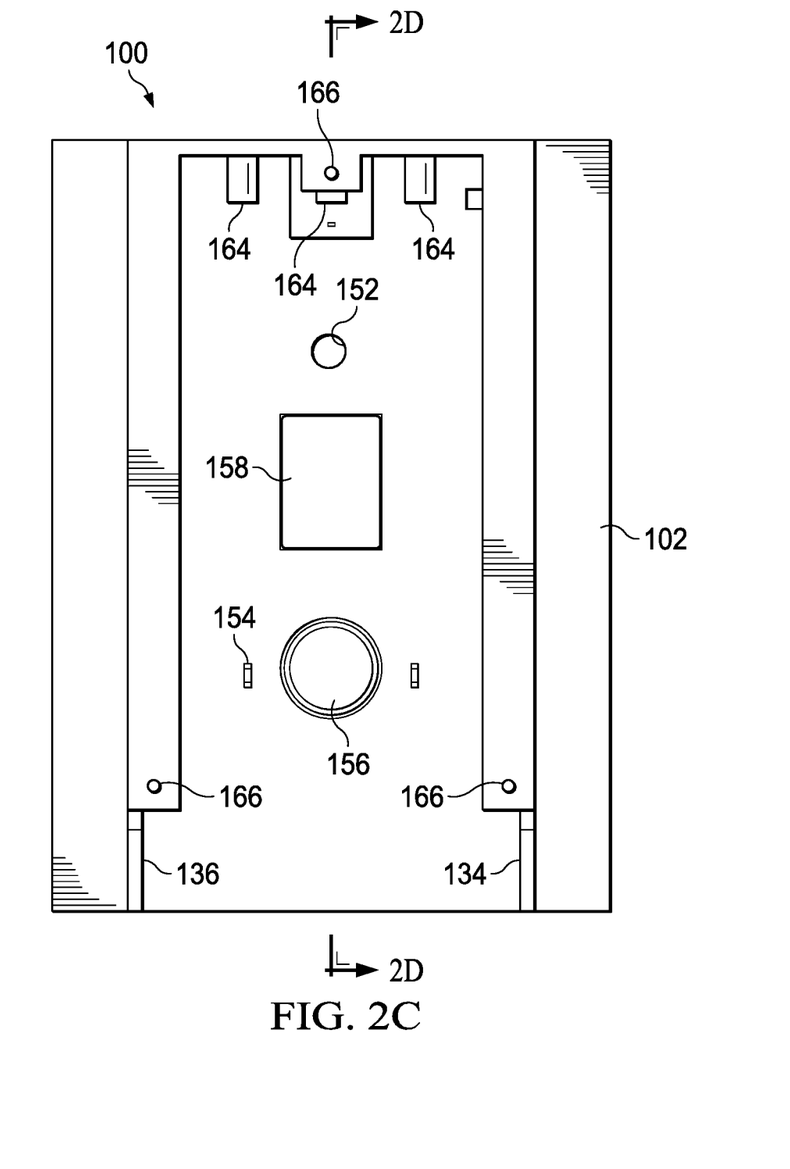
Figure 2D:
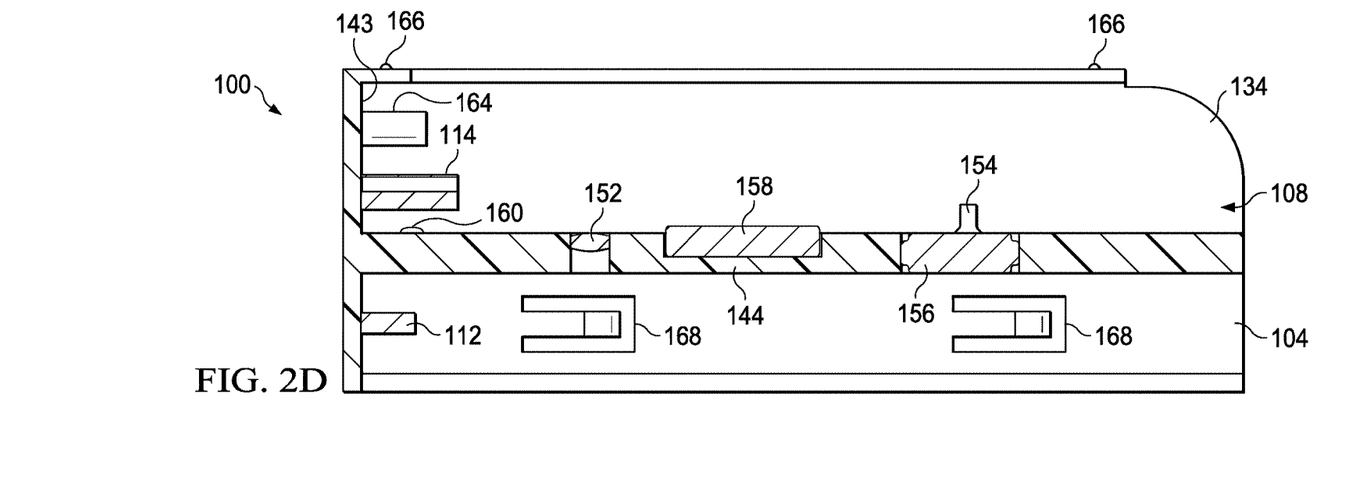
FIG. 2d is a side, section view of the specimen delivery cartridge of FIG. 2a, taken along the line 2D-2D of FIG. 2c.

Referring now to FIG. 1, in an illustrative embodiment, a mating adaptor 100 includes an adaptor body 102 that is sized and configured to receive and pair a computing device 106 and a specimen delivery cartridge 110. The adaptor body 102 has a first receiving area 104 that is sized and configured to receive the computing device 106, which may be, for example, a popular smart phone. The adaptor body 102 also has a second receiving area 108 that is sized and configured to receive the specimen delivery cartridge 110. The aforementioned pairing results in one or more of a physical coupling, optical coupling, thermal coupling, communicative coupling, or electrical coupling between the computing device 106 and the specimen delivery cartridge 110.

The adaptor 100 is operable to allow a user to operate the specimen delivery cartridge 110 to carry out a diagnostic process, such as testing a biological specimen carried within a compartment of the specimen delivery cartridge 110 for a particular target pathogen or set of pathogens (i.e., one or more pathogens that are sought to be detected). For example, the diagnostic process may include testing a blood or saliva swab for a virus, such as influenza or Ebola. To facilitate communication between the computing device 106 and specimen delivery cartridge 110, the first receiving area 104 may include a first connector 112, which may be the male portion of a device connector. Similarly, the second receiving area may include a corresponding connector that couples to the specimen delivery cartridge 110, which may be a male portion of a cartridge connector. Examples of such connectors include, without limitation, an audio (stereo) jack, a proprietary data or power connector, or a type of USB connector.

In the disclosed diagnostic system that includes the mating adaptor 100, computing device 106, and specimen delivery cartridge 110, physical coupling provided by the mating adaptor may also provide for the exchange of electrical or optical signals between the computing device 106 and specimen delivery cartridge 110.

In an embodiment, the receiving areas of the mating adaptor 100 are configured to allow a user to slide or insert the computing device 106 and specimen delivery cartridge 110 into the first receiving area 104 and second receiving area 108, respectively. Snap-in or plug-in engagement may also be accomplished using the connectors or by including additional snap or plug features in the adaptor body 102 and in the bodies of the computing device and device 106 and specimen delivery cartridge 110. This simplified coupling between the mating adaptor 100, computing device 106 and specimen delivery cartridge 110 allows for the devices to be assembled together using only very basic skills.

Owing to the enormous amount of research and development funds invested in the development of smartphones and other computing devices, certain capabilities exist with such devices that are potentially useful for biological detection and clinical diagnostics. Capabilities that an off-the-shelf smartphone lacks, however, are the abilities to directly manipulate fluids within its existing form factor and to accept bodily fluid specimens directly for analysis. In an illustrative embodiment, the specimen delivery cartridge 110 provides a mechanism for accepting fluid specimens and manipulating fluid to carry out a diagnostic process. The mating adaptor provides an interface between the specimen delivery cartridge 110 and the computing device 106, effectively providing the computing device with the additional functionality needed to manipulate and analyze a fluid specimen.

The specimen delivery cartridge 110 may generally be understood to be a consumable or "single-use" cartridge suitable for accepting and housing a wide variety of human, animal, agricultural, or environmental specimens for assaying. This assaying may involve some or all of the following steps: the introduction of additional biochemical reagents to specimen fluids; the mixing and agitation of said fluids; the heating of various but specific fluids for distinct periods of time (known commonly as incubation); the use of filters; and the use of various types of particles.

The mating adaptor 100 couples the specimen delivery cartridge 110 with a computing device 106, as shown in an operational configuration in FIG. 1. The mating adaptor 100 allows for the seamless integration of the specimen delivery cartridge 110 with the computing device 106. In a preferred embodiment, electrical, mechanical, and optical interfaces exist between the mating adaptor 100 and the specimen delivery cartridge 110 and computing device 106 to facilitate operation of the devices, as described in more detail below.

In some embodiments, the specimen delivery cartridge 110 is a sealable device that may receive and process a fluid specimen without exposing the computing device 106 or adaptor 100 to the fluid specimen. As a result, fluids, including reagents, specimens and any other liquid materials are safely contained internal to the specimen delivery cartridge 110 following harvesting, and there is no fluid flow between the specimen delivery cartridge 110 and any other components. The mating adaptor 100 shown here is illustrative only and different versions of the mating adaptor 100 may be fabricated to accommodate different types of computing devices on the market. In an embodiment, the computing device 106 is a smart phone, and it is noted that the first receiving area 104 that receives the computing device 106 may be made in any number of dimensional configurations, each corresponding to a unique smart phone. Similarly, the mating adaptor 100 accommodates any specimen delivery cartridge 110, regardless of the type of specimen used or assay format. In this sense, the mating adaptor 100 may serve as a universal coupling between a specimen delivery cartridge 110 and a computing device 106.

Referring now primarily to FIGS. 2a-2d, the mating adaptor 100 includes an adaptor body 102 having a first receiving area 104 for receiving the computing device 106 and a second receiving 108 area for receiving the specimen delivery cartridge 110. The first receiving area 104 includes a first, device connector 112 corresponding to a computing device connector, which may be an audio jack, Lightning®, USB, microUSB, miniUSB, or any other suitable connector. The second receiving area 108 includes a second connector 114 corresponding to a specimen delivery cartridge connector. The second connector 114 is shown here as a USB connector, but may similarly be an audio jack, USB, microUSB, miniUSB, or any other suitable connector.

The mating adaptor body 102 may be fabricated from plastic, polymer, metal, or one of many possible composite materials. The selected material has an appropriate amount of rigidity and elasticity to facilitate reliable and releasable attachment to a computing device 106 through the first receiving area 104, and to allow insertion into the mating adaptor 100 of the specimen delivery cartridge 110 at a second receiving area 108. Guide rails 146 allow for the precise positioning of the cartridge into the second receiving area 108. The guide rails 146 consist of a top lip and sides into which the specimen delivery cartridge 110 slides to establish a secure fit to the mating adaptor 100. The guide rails 146 also provide a stable and mechanically secure connection.

At one end of the guide rails 146 there is an opening to allow the SDS to be placed into receiving area 108. At another end of the guide rails 146 there are stops or a stopping feature such as a connector, backplane, or backstop. In one embodiment the stops are "L-shaped" bracket surfaces at the ends of the rails to prevent further sliding of the mating adaptor 100. In another embodiment, the base 143 of the mating adaptor 100 forms a complete backplane or backstop to the second receiving area 108.

Referring again to FIGS. 2a-2d, the first receiving area 104 has an open end and a closed end, with the device connector 112 being positioned within the closed end. The first receiving area 104 has a width spanning from a first lateral surface 116 to a second lateral surface 118. That width is substantially equal to the width of the computing device. The first receiving area 104 also has a depth that spans from a rear surface 122 to an inner surface of a retainer 120. The depth is substantially equal to the thickness of the computing device. It is expressly contemplated that any number of suitable embodiments may be fabricated to accommodate different makes and models of computing devices, which may include popular smart phones, personal digital assistants, or other more purpose-specific computing devices, and that the mating adaptor may be sized and configured to interface with each such computing device. The depth, width, connector position, and position of other elements of the mating adaptor that correlate to features of the computing devices may therefore be alternatively positioned or sized and configured in each embodiment of the mating adaptor to accommodate and interface with the applicable computing device.

To retain the computing device within the first receiving area 104, the mating adaptor may include or be formed from a compressive material at the first receiving area 104 to accommodate an interference fit that secures the computing device within the first receiving area 104. In addition, the first receiving area 104 may be tapered such that the width of the first receiving area 104 is narrower at a bottom surface than at a top surface or opening, and/or wherein the width at the bottom surface is nominally less than the width of the computing device at base of the computing device 106 that includes the computing device connector 112. In such an embodiment, the interference fit results in deformation of the compressive material, which in turn results in the first lateral surface 116 and second lateral surface 118 exerting a retaining force on the computing device to retain the computing device in the first receiving area 104. The mating adaptor 100 may also (or alternatively) be formed such that the depth of the first receiving area 104 is narrower at a bottom surface than at a top surface, and wherein the depth at the bottom surface is nominally less than the thickness of the computing device 106 to generate a similar interference fit. In some embodiments, the mating adapter 102 includes tabs 168 that engage the surface of the computing device 106 and are deformed outward by the computing device 106 when the computing device 106 is inserted into the mating adaptor 102. In such embodiments, the spring force of the tabs 168 helps to retain the computing device 106 within the first receiving area 104 of the mating adaptor 102.

In some embodiments, first receiving area 104 has a height extending from a bottom surface 124 to a top surface 126 that is substantially equal to the height of the computing device. In such embodiments, the mating adaptor 100 may further include a retaining clip that partially extends over a top surface of the computing device 106 to retain engagement at the computing device connector 112 when the computing device 106 is inserted into the first receiving area 104. The clip may be, for example, a spring loaded retaining clip that is biased in the engaged position.

The mating adaptor 100 also includes a number of other features that facilitate interaction between the computing device 106 and the specimen delivery cartridge 110. For example, as shown in FIGS. 2a-2d, the mating adaptor 100 includes a specimen delivery cartridge connector 114, a pressure sensor 160, an optical interface 152, a thermal pad 158, a magnet 156, and a mechanical actuator 154, shown here in the form of two protruding posts. In addition or in the alternative to the mechanical actuators 154, the mating adapter may include one or more actuation posts 164 to actuate fluid dispensing components of a specimen delivery cartridge 110.

The optical interface 152 is positioned to align with an optical interface of the specimen delivery cartridge 110. The optical interface 152 provides a path for light to be transmitted from a viewport or optical outlet of the specimen delivery cartridge 110 to a lens or optical inlet of the computing device 106. To that end, the mating adaptor 100 may be sized and configured to align a lens of a camera or image processing sensor of the computing device 106 with the viewport of the specimen delivery cartridge 110. In another embodiment, the optical interface 152 includes an optically transmissive component, such as a light pipe, to transmit light from the viewport of the specimen delivery cartridge 110 to the lens or image sensor of the computing device 106 for processing. As referenced here, optically transmissive means that the component is operable to facilitate the transmission of photons from a light emitting source to a light receiving sensor or lens. In an embodiment, the optical interface 152 includes an optical element, which may be a lens, a series of lenses, an optical coating, or a combination of the foregoing.

In an embodiment, the optical interface 152 of the mating adaptor 100 is positioned proximate a testing chamber of the specimen delivery cartridge 110, in which a chemi-luminescent process may be executed and observed, or in which a fluorescent detection test may be executed, to determine whether a target pathogen is present in the specimen. In such an embodiment, the optical interface 152 is operable to transmit light from the chemi-luminescent process to a lens or image sensor of the computing device 106. The image sensor may be a CCD image sensor, CMOS image sensor, or any other suitable imaging system.

In an embodiment, the mating adaptor 100 may include an electrical interface, such as one or more conductive probes, capable of enabling a capacitance or resistance measurement of a test chamber of the specimen delivery cartridge 110. The electrical interface may include one or more conductive elements that coupled to complementary conductive elements of the specimen delivery cartridge to act as a conductive probe of the test chamber. In such an embodiment, the mating adaptor 100 may further include an electronic sensor, such as a MOSFET, other field-effect transistor, or other circuitry to perform an electronic test using the associated specimen delivery cartridge 110.

The thermal pad 158 is positioned to align with a portion of the specimen delivery cartridge 110 that includes a specimen and is operable to heat the specimen in response to a signal received from the computing device 106 to facilitate the processing of a specimen. As noted above, this heating process may be referred to as incubation. The magnet 156 is similarly positioned to align with a portion of the specimen delivery cartridge 110 that includes magnetic particles, and is operable to manipulate the magnetic particles in accordance with a processing step for processing a specimen in the specimen delivery cartridge 110. The magnet 156 may be an electromagnet actuated by the computing device 106, or a permanent magnet. In an embodiment in which the magnet 156 is a permanent magnet, the mating adaptor 100 may further include a movable magnetic shield. The movable magnetic shield may be manipulated by the computing device 106 using a control system, or by a manual user operation (e.g., manually displacing the shield in response to an instruction delivered to a user from the computing device 106). In either case, a magnetic field emitted by the magnet 156 may be selectively interacted with the specimen delivery cartridge 110 for (for example) the purposes of processing a specimen. In an embodiment in which the magnet 156 is an electromagnet, the magnet 156 may comprise a plurality of selectively actuatable electromagnets that can be selectively activated to generate magnetic fields having alternating origins.

The mating adaptor 100 also includes the actuator 154 and sensor 160. The sensor 160 may be, for example, an optical sensor or a pressure sensor, and may be operable to determine whether a specimen delivery cartridge 110 is present within the second receiving area 108. Further, it is noted that while the sensor 160 is shown as being positioned on the back surface 144 of the mating adaptor 100, the sensor 160 may alternatively be positioned on the base surface 143 adjacent the specimen delivery cartridge connector 114 or any other surface of the second receiving area 108.

Also positioned on the back surface 144 of the mating adaptor 100 is the actuator 154, which may include one or more actuator posts. The actuator 154 is operable to actuate a process of the specimen delivery cartridge 110 in response to an actuation criterion. The actuation criteria may be one or more of the following: (1) detection of the specimen delivery cartridge in the second receiving area 108, (2) detection of the computing device 106 in the first receiving area 104, (3) a user input received via the computing device 106, (4) an automatically generated actuation signal generated in response to a process output generated by the computing device 106, or (5) any other suitable actuation criteria. In an embodiment, the actuator 154 provides a method for transmitting a mechanical actuation signal to initiate fluidic, mechanical, electrical or optical processes useful to the successful completion of a given biological test (or assay). For example, the actuator 154 may initiate a plunger within the specimen delivery cartridge 110 to initiate a fluidic process, such as the release of a reagent or other fluid. In an embodiment, the actuator 154 posts may align with receptacles in the specimen delivery cartridge 110 that house or provide access to compressible areas that may be compressed by the actuator 154 to move or deploy material (for example, a wash fluid or reagent) within the specimen delivery cartridge 110.

In some embodiments, the mating adapter 102 includes actuation posts 164 (in addition or in the alternative to the mechanical actuators 154) actuate fluid dispensing components of a specimen delivery cartridge 110 upon insertion into the mating adapter 102.

In the case of some assaying processes, a vibration inducing component of the computing device 106 may be used to agitate or vibrate the specimen delivery cartridge 110. To facilitate such agitation or vibration, the mating adapter may include isolation supports 166, which may comprise flexible, rounded or pointed nubs, or similar supports that isolate the mating adapter 102 from a supporting surface and reduce impedance to vibration that might otherwise be exerted on the mating adapter 102 by the supporting surface. In the illustrated embodiment, the isolation supports 166 are positioned on an outer surface 140 of the mating adaptor body 102, which is parallel to and offset from the back surface 144. In some embodiments, the isolation supports 166 may be positioned on the opposing outer surface of the mating adapter body 102 adjacent to the first receiving area 104.

Figure 3:
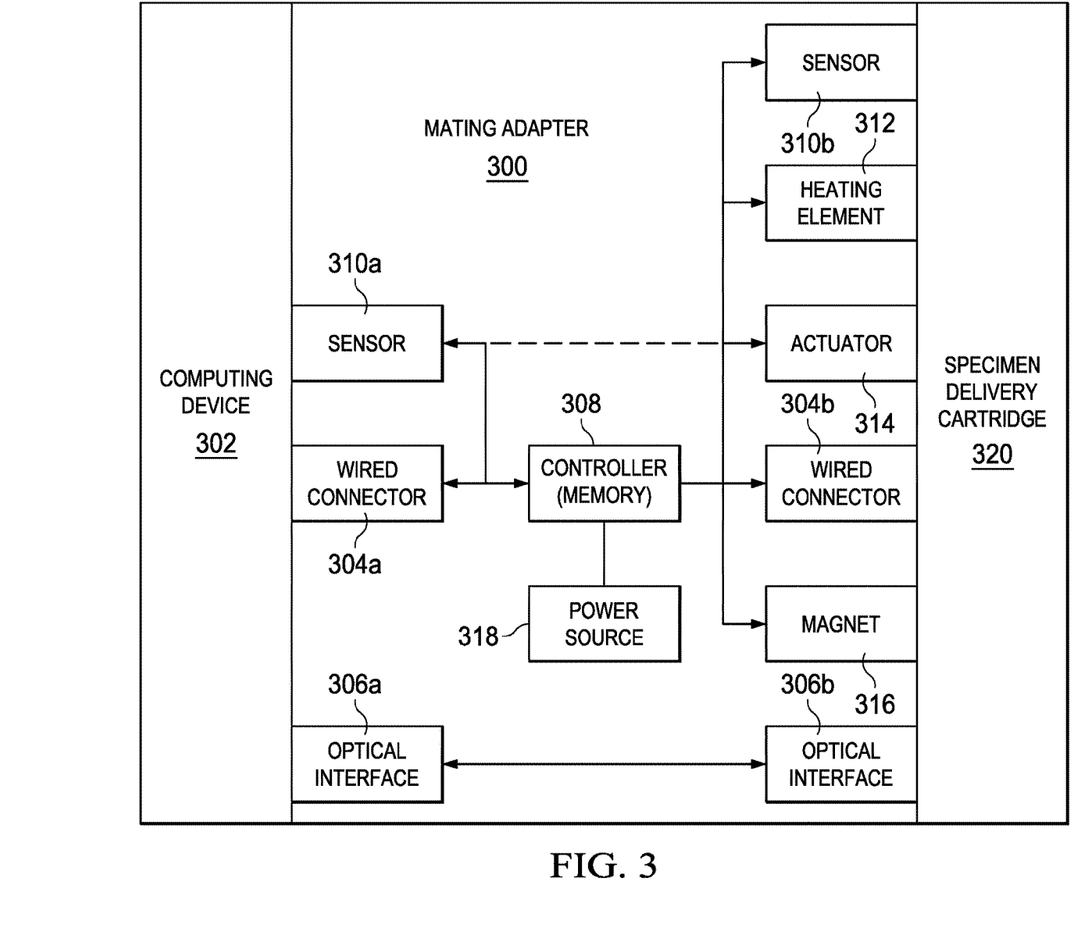
FIG. 3 is a block diagram showing the components of a mating adaptor (analogous to the mating adaptor of FIG. 1) in relation to a coupling between a computing device and a specimen delivery cartridge.

FIG. 3 is a block diagram that schematically illustrates the components of the mating adaptor 300 as they relate to the coupling between the computing device 302 and specimen delivery cartridge 320. The mating adaptor 300 is analogous to the mating adaptor 100 described with regard to FIGS. 1 and 2a-2d. Similarly, the computing device 302 is analogous to the computing device 106 and the specimen delivery cartridge 320 is analogous to the specimen delivery cartridge 110.

The mating adaptor 300 includes a first wired connector 304a that couples to a data port, audio port, or powered port of the computing device 302. The mating adaptor 300 may also include a sensor 310a that is operable to detect the presence of the computing device 302 or is otherwise operable to determine whether the computing device 302 is coupled to the mating adaptor 300. Similarly, the mating adaptor 300 may include a sensor 310b that is operable to determine whether the specimen delivery cartridge 320 is coupled to the mating adaptor 300. In an embodiment, the mating adaptor 300 may also provide a passive optical interface or optical coupling that includes a computing device-side optical interface 306a and a cartridge-side optical interface 306b. The optical coupling may result from alignment of an optically transmissive element of the mating adaptor 300, and an optical component of the computing device 302, an optical component or viewable area of the specimen delivery cartridge 320. Alternatively, a light pipe may be used to form the optical interface coupling, which may (in such an embodiment) follow a circuitous path from the cartridge-side optical interface 306b to the computing device-side of the optical interface 306a to account for misalignment.

In an embodiment, the mating adaptor 300 includes an optional controller 308 that provides for an intelligent coupling between the computing device 302 and specimen delivery cartridge 320. The controller 308 may include a memory and a power source 318. The controller 308 may be operable to actuate or control a number of features of the specimen delivery cartridge 320 based on an input signal. The input signal may be generated by user input received at the mating adaptor 300, input received from the computing device 302 via the wired connector 304a (which may be user input received from a graphical user interface of the computing device), or a sensor input received from sensor 310a. For example, the input may be used to actuate one or more of a heating element 312, an actuator 314, a controllable magnet 316, and a vibrating component or agitator. In other embodiments, the controller 308 may be omitted and any one of the foregoing components may be actuated based on the sensor 310 detecting the presence of the computing device 302 and/or the sensor 310b detecting the coupling of the specimen delivery cartridge 320 to the mating adaptor 300.

As noted above, the mating adaptor 300 provides a mechanism to either actuate or enable fluidic, mechanical, electrical or optical processes useful to the successful completion of a given biological test. In operation, to link the computing device 302 to a specimen delivery cartridge 320, a user or operator first slides the mating adaptor 300 over the computing device 302. This is a simple action that requires no special training and is intuitively executed from the shape of the adaptor and other components. To prompt the user to take the correct action in forming the link, a visual indicator, such as an arrow pointing in the direction the computing device 106 is included on the surface of the mating adaptor 300 to facilitate engagement of the mating adaptor 300. Similarly, a written instruction may also be embossed on the mating adaptor 300 to ensure complete clarity. In another embodiment, the features of the computing device 302 (e.g., a communication system, analytical components, and a graphical user interface, may be integrated with the mating adaptor 300 as a single component).

In view of the foregoing, the present disclosure provides for a mating adaptor that allows a user to execute processes relating to an assay using their smart phone and a mating adaptor (1) to heat or incubate a test specimen, (2) to actuate mixing, movement, or reactive processes via vibration or via a mechanical actuator, (3) to deliver or receive an electronic signal, (4) to actuate or manipulate a magnetic field, (5) to actuate a plunger mechanism. In addition the mating adaptor may include an optical interface between a computing device and test chamber of the specimen delivery cartridge to view, for example, chemi-luminescence indicating the result of a diagnostic process.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

What is claimed is:

1. A mating adaptor comprising:
   an adaptor body having a first receiving area for receiving a computing device and a second receiving area for receiving a specimen delivery cartridge; and
   one or more actuation posts extending from a surface of the adaptor body, the actuation posts being operable to actuate fluid dispensing components of a specimen delivery cartridge;
   wherein the first receiving area comprises a first connector corresponding to a computing device connector;
   wherein the second receiving area comprises a second connector corresponding to a specimen delivery cartridge connector, and
   wherein the first receiving area comprises an open end and a closed end, the closed end comprising the first connector.

2. The mating adaptor of claim 1, wherein:
   the first receiving area has a width spanning from a first lateral surface to a second lateral surface that is substantially equal to the width of the computing device; and
   the first receiving area has a depth spanning from a rear surface to an inner surface of a retainer that is substantially equal to the thickness of the computing device.

3. The mating adaptor of claim 2, wherein the mating adaptor comprises a plurality of tabs that protrude into the first receiving area, and wherein insertion of the computing device into the first receiving area results in deformation of the tabs and the corresponding exertion of a retaining force on the computing device to retain the computing device in the first receiving area.

4. The mating adaptor of claim 1, further comprising an actuator for transmitting a mechanical actuation signal to initiate a fluidic process of a specimen delivery cartridge, wherein the second receiving area comprises an open end and a closed end, and wherein the actuator comprises a protrusion extending from a surface that is adjacent to the closed end of the second receiving area.

5. The mating adaptor of claim 2, further comprising a plurality of isolation supports positioned on an outer surface of the mating adaptor.

6. The mating adaptor of claim 1, further comprising an optical interface extending through a rear surface of the first receiving area and positioned to align an image sensor of the computing device with an optical interface of the specimen delivery cartridge.

7. The mating adaptor of claim 6, wherein:
   the optical interface comprises a lens assembly;
   the optical interface is positioned proximate a testing chamber of the specimen delivery cartridge; and
   the lens assembly is operable to transmit light emissions from the testing chamber to the image sensor of the computing device.

8. The mating adaptor of claim 1, wherein:
   the second receiving area comprises an open end and a closed end, the closed end comprising the second connector,
   the second receiving area has a width spanning from a third lateral surface to a fourth lateral surface that is substantially equal to the width of the specimen delivery cartridge; and the second receiving area has a depth spanning from a second rear surface to an inner surface of a retainer that is substantially equal to the thickness of the specimen delivery cartridge.

9. The mating adaptor of claim 8, wherein the third lateral surface and the fourth lateral surface comprise a retaining feature that complements a retaining feature of the specimen delivery cartridge to retain engagement between the specimen delivery cartridge and the second connector.

10. The mating adaptor of claim 8, wherein the mating adaptor comprises a controller operable to electronically control a component of a specimen delivery cartridge based on electronic input received from the computing device.

11. The mating adaptor of claim 10, wherein the component is selected from the group consisting of a heating element, an actuator, and a magnet.

12. The mating adaptor of claim 1, wherein each actuation post comprises a protrusion extending from the closed end of the second receiving area.

13. A method of operating a mating adaptor, the method comprising:
sliding a computing device into a first receiving area of a mating adaptor, the mating adaptor comprising an adaptor body having the first receiving area for receiving a computing device and a second receiving area for receiving a specimen delivery cartridge, and one or more actuation posts extending from a surface of the adaptor body, the actuation posts being operable to actuate fluid dispensing components of a specimen delivery cartridge, wherein the first receiving area comprises a first connector corresponding to a computing device connector, wherein the second receiving area comprises a second connector corresponding to a specimen delivery cartridge connector, and wherein the first receiving area comprises an open end and a closed end, the closed end comprising the first connector,
wherein the method further comprises sliding a specimen delivery cartridge into a second receiving area of the mating adaptor,
wherein sliding the computing device into the first receiving area comprises coupling a data port of the computing device to a first connector of the mating adaptor, and
wherein sliding the specimen delivery cartridge into the second receiving area comprises coupling a second data port of the specimen delivery cartridge to a second connector of the mating adaptor.

14. The method of claim 13, further comprising operating the computing device to control a component of the specimen delivery cartridge, the component being selected from the group consisting of a heating element, an actuator, and a magnet.

15. The method of claim 13, further comprising receiving an image from the specimen delivery cartridge via an image sensor of the computing device via an optical interface extending through a rear surface of the first receiving area.

* * * * *